(12) United States Patent
Budagher

(10) Patent No.: US 10,716,730 B2
(45) Date of Patent: Jul. 21, 2020

(54) GAZE STABILIZATION SYSTEM AND METHOD

(71) Applicant: Ovard, LLC, Dallas, TX (US)

(72) Inventor: Michael Budagher, Dallas, TX (US)

(73) Assignee: OVARD, LLC, Dallas, TX (US)

( * ) Notice: Subject to any disclaimer, the term of this patent is extended or adjusted under 35 U.S.C. 154(b) by 386 days.

(21) Appl. No.: 14/818,042

(22) Filed: Aug. 4, 2015

(65) Prior Publication Data

US 2016/0213551 A1    Jul. 28, 2016

Related U.S. Application Data

(60) Provisional application No. 62/106,646, filed on Jan. 22, 2015.

(51) Int. Cl.
*A61H 5/00* (2006.01)
*A61B 3/113* (2006.01)
*A61H 1/02* (2006.01)
*A61B 3/00* (2006.01)
(Continued)

(52) U.S. Cl.
CPC ............ *A61H 5/00* (2013.01); *A61B 3/113* (2013.01); *A61H 1/0296* (2013.01); *A61B 3/0091* (2013.01); *A61B 5/0496* (2013.01); *A61B 5/4023* (2013.01); *A61H 2201/1607* (2013.01); *A61H 2201/5035* (2013.01); *A61H 2201/5043* (2013.01); *A61H 2201/5061* (2013.01);
(Continued)

(58) Field of Classification Search
CPC ........ A61H 5/00; A61H 5/005; A61H 5/0496; A61H 5/4863; A61H 1/0296; A61H 2201/1607; A61H 2201/5035; A61H 2201/5043; A61H 2201/5061; A61H 2201/5084; A61H 2201/5092; A61H 2203/0431; A61B 3/0091; A61B 3/113; A61B 5/0496; A61B 5/4023
See application file for complete search history.

(56) References Cited

U.S. PATENT DOCUMENTS 4,278,249 A * 7/1981 Forrest ................. A63B 23/025
                                                            482/10
4,710,128 A   12/1987 Wachsmuth
(Continued)

FOREIGN PATENT DOCUMENTS

DE    102004020817 A1    12/2005
WO    2004/043257 A1      5/2004
(Continued)

OTHER PUBLICATIONS

English translation of DE102004020817A1, published Dec. 8, 2006 (10 pages).
(Continued)

*Primary Examiner* — Nyca T Nguyen
(74) *Attorney, Agent, or Firm* — James R. Gourley; Carstens & Cahoon, LLP

(57) ABSTRACT

A system and method are provided that allow a practitioner to rotate a human subject's head in three-dimensional space using a robotic arm with a head mount attached to one end, while the subject is focused on a visual target. The robotic arm is controlled by a computer system operatively coupled to the various sensors and drive motors embedded with the robotic arm.

10 Claims, 4 Drawing Sheets

(51) Int. Cl.
*A61B 5/00* (2006.01)
*A61B 5/0496* (2006.01)

(52) U.S. Cl.
CPC ............ *A61H 2201/5084* (2013.01); *A61H 2201/5092* (2013.01); *A61H 2203/0431* (2013.01)

(56) References Cited

U.S. PATENT DOCUMENTS

| | | | | |
|---|---|---|---|---|
| 4,954,815 | A * | 9/1990 | Delmonte | A63B 23/025 128/866 |
| 5,137,015 | A * | 8/1992 | Anglehart | A61H 1/0296 297/408 |
| 5,303,715 | A * | 4/1994 | Nashner | A61B 5/1036 600/559 |
| 5,491,757 | A * | 2/1996 | Lehmer | A61B 3/0083 348/78 |
| 5,725,435 | A | 3/1998 | DeCastro Faria | |
| 6,551,214 | B1 | 4/2003 | Taimela | |
| 6,770,082 | B2 * | 8/2004 | Dominguez | A61B 90/14 606/130 |
| 6,798,443 | B1 | 9/2004 | Maguire | |
| 6,800,062 | B2 | 10/2004 | Epley | |
| 7,559,766 | B2 | 7/2009 | Epley | |
| 7,691,073 | B2 * | 4/2010 | Naganuma | A61B 5/00 601/89 |
| 8,529,463 | B2 | 9/2013 | Santina | |
| 8,585,609 | B2 * | 11/2013 | Kiderman | A61B 3/113 600/558 |
| 8,702,631 | B2 * | 4/2014 | Maher | A61B 5/11 601/24 |
| 8,868,373 | B2 | 10/2014 | Eng | |
| 9,277,857 | B1 * | 3/2016 | Berme | A61B 3/09 |
| 2002/0151818 | A1 * | 10/2002 | Watt | A61B 5/0496 600/552 |
| 2003/0028130 | A1 * | 2/2003 | Wunderly | A61H 1/0274 601/5 |
| 2004/0015098 | A1 * | 1/2004 | Souvestre | A61B 3/113 600/558 |
| 2004/0061831 | A1 | 4/2004 | Aughey | |
| 2008/0272265 | A1 | 11/2008 | Ciesielka | |
| 2011/0028872 | A1 * | 2/2011 | Kevin | A61B 5/11 601/86 |
| 2012/0253241 | A1 | 10/2012 | Levital | |
| 2013/0021578 | A1 * | 1/2013 | Chen | G06K 9/00604 351/209 |
| 2014/0087340 | A1 | 3/2014 | Maher | |
| 2014/0192326 | A1 | 7/2014 | Kiderman | |
| 2016/0242642 | A1 * | 8/2016 | Migliaccio | A61B 3/113 |

FOREIGN PATENT DOCUMENTS

| | | |
|---|---|---|
| WO | 2007/138598 A2 | 12/2007 |
| WO | 2013/140406 A1 | 9/2013 |

OTHER PUBLICATIONS

English translation of WO2004/043257A1, published May 27, 2004 (11 pages).
International Search Report and Written Opinion of the ISA from PCT/US2016/013800 dated Mar. 30, 2016 (8 pages).
International Search Report and Written Opinion of the ISA from PCT/US2016/013798 dated Mar. 25, 2016 (6 pages).
International Search Report and Written Opinion of the ISA from PCT/US2016/013803 dated Mar. 11, 2016 (7 pages).
International Search Report and Written Opinion of the ISA from PCT/US2016/013802 dated Mar. 30, 2016 (7 pages).

* cited by examiner

GAZE STABILIZATION SYSTEM AND METHOD

CROSS-REFERENCE TO RELATED APPLICATION

This application claims priority to co-pending U.S. Provisional Patent Application Ser. No. 62/106646 filed on Jan. 22, 2015, and entitled "PATIENT ROBOT-MEDICAL DEVICE CONCEPT" the technical disclosure of which is hereby incorporated by reference in its entirety.

BACKGROUND OF THE INVENTION

1. Technical Field

The present invention relates to a system and method for manipulating the orientation and position of a human subject's head, and more particularly a system and method that allows a practitioner to rotate and position the head of a human subject in space in order to diagnose or treat the human body.

2. Description of Related Art

Many patients with brain injuries, neurodevelopmental disorders, or neurodegenerative disorders have impaired motor and cognitive capabilities. It is well evidenced that basic and complex motor and cognitive functions have direct and indirect dependencies on head, neck, and ocular movements. The vestibular and visual/ocular organs are primary sensors, which help our brain understand our spatial orientation and how to interact in our environment. The ability to measure head, neck, and eye movements and quantify deficiencies enables an opportunity to therapeutically rehabilitate these organs and improve human performance Systems for rotating a human body for the purpose of diagnosing and treating the human vestibular system are known in the art. U.S. Pat. Nos. 6,800,062, 7,559,766 and 8,702,631 all describe such systems. However, none of those systems are capable of moving or positioning the human subject's head in three dimensional space along every possible vector without limitation, while the human body is stationary. As described below in the detailed written description, the system of the present invention implements several different features and technologies that differentiate it from the prior art.

SUMMARY OF THE INVENTION

In one embodiment, a method of treating at least one system of a human subject comprises: arranging a human subject within a human receiving area facing a visual target; securing a head mount to the human subject's head, wherein the head mount is affixed to and actuated by a distal end of a robotic arm, wherein the distal end is opposite of a base of the robotic arm; actuating the head mount to move the human subject's head or sense movement of a human subject's head in three dimensional space while the human subject focuses on the visual target.

In another embodiment according to one or any combination of other embodiments, the system is a vestibular system. In another embodiment according to one or any combination of other embodiments, the system is a visual system. In another embodiment according to one or any combination of other embodiments, the system is a proprioceptive system. In another embodiment according to one or any combination of other embodiments, the visual target is stationary during the actuating. In another embodiment according to one or any combination of other embodiments, the visual target is moving during the actuating.

In another embodiment according to one or any combination of other embodiments, the method further comprises the step of collecting data indicative of the position or movement of the human subject's eyes. In another embodiment according to one or any combination of other embodiments, the method further comprises the step of collecting data indicative of the position or movement of the human subject's head.

In another embodiment according to one or any combination of other embodiments, the system is at least one of a vestibular system, a visual system, and a proprioceptive system. In another embodiment according to one or any combination of other embodiments, the human subject is seated during the method.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
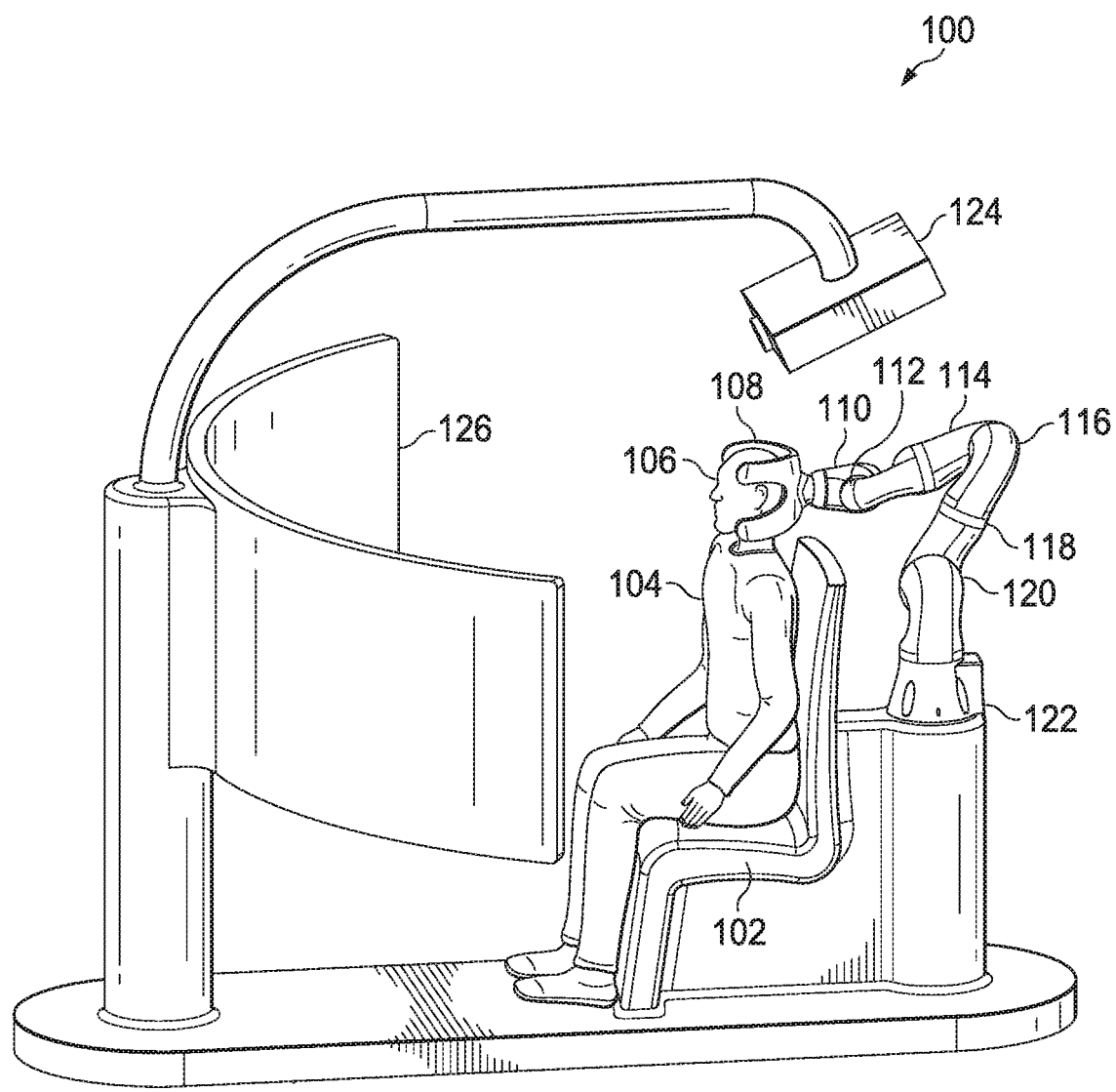
FIG. 1 illustrates a front perspective view of one embodiment of the head manipulation device of the present invention.
Figure 2:
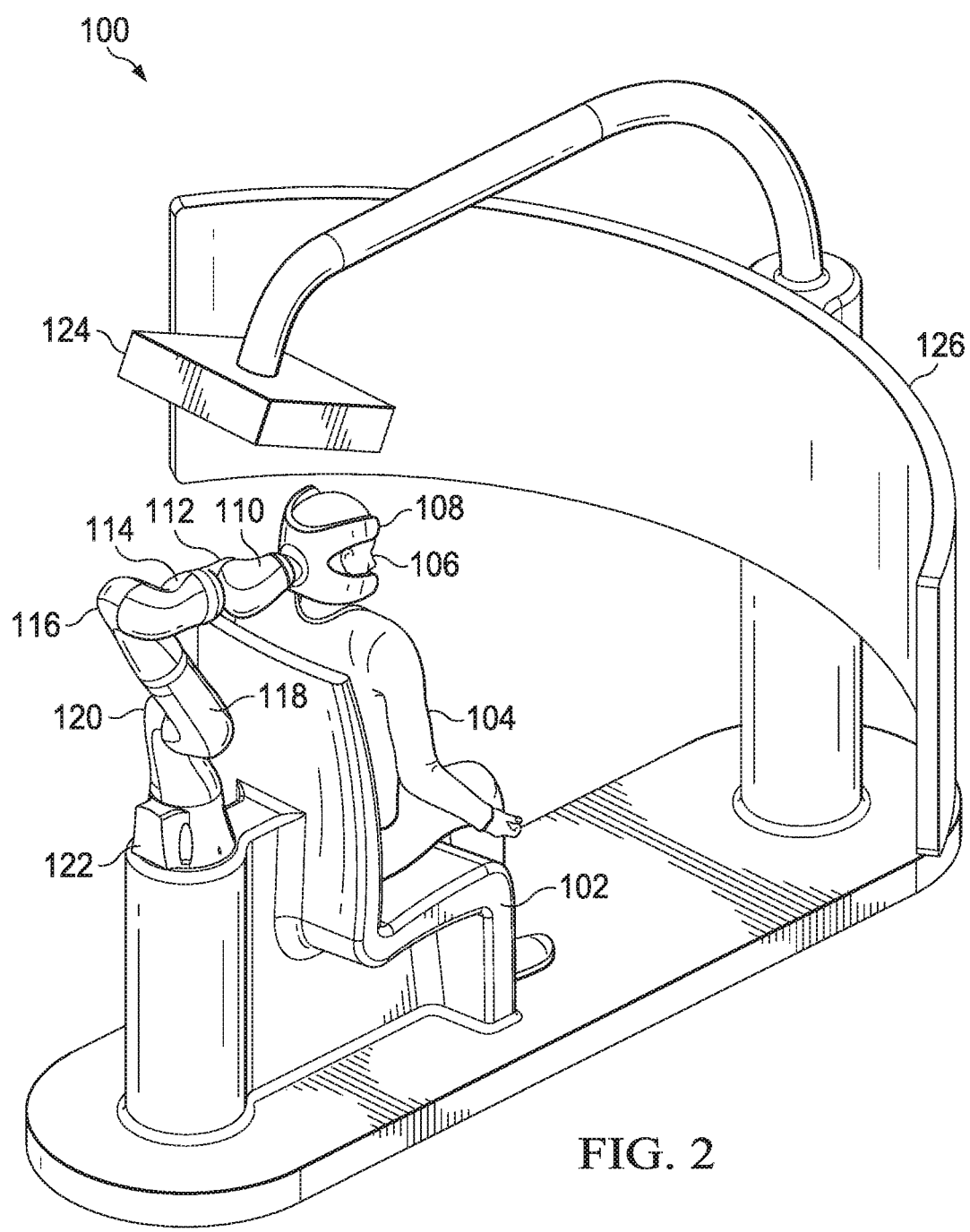
FIG. 2 illustrates a back perspective view of one embodiment of the head manipulation device of the present invention.

FIG. 1 depicts a perspective view of one embodiment of the human head manipulation apparatus 100 of the present invention. Generally, the system comprises a seat or chair 102 configured to provide support to a human subject 104 seated thereon. A head mount 108 is temporarily affixed to the human subject's head 106. Movement of the head mount 108 manipulates the motion vector, position and angle of the human subject's head 106 in three-dimensional space.

Figure 4:
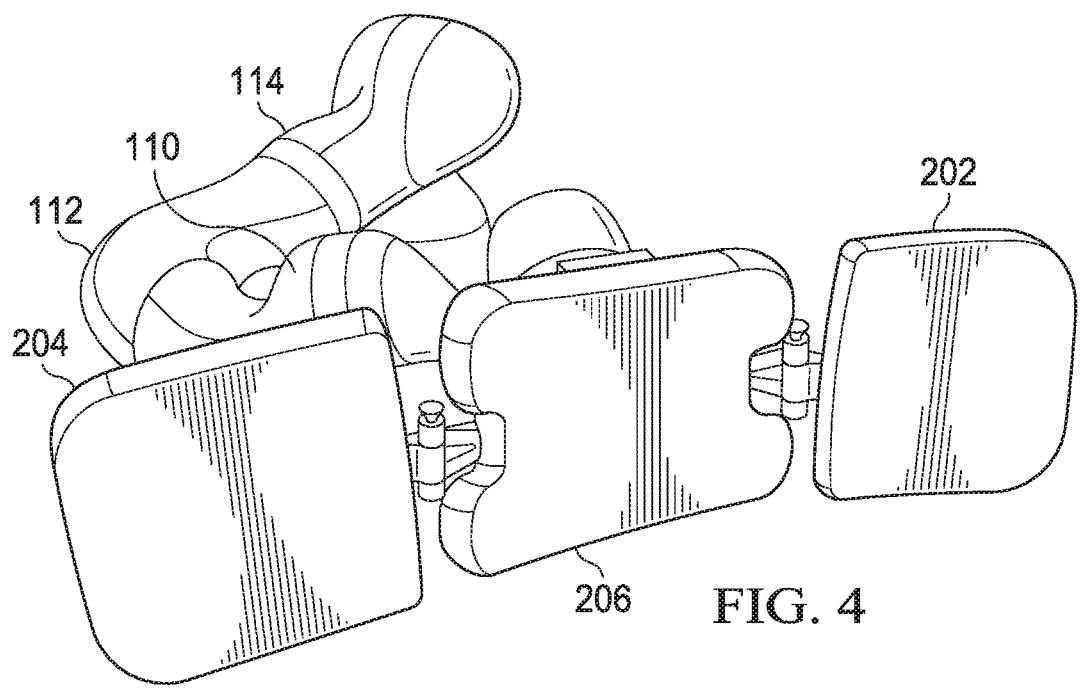
FIG. 4 illustrates a perspective view of another embodiment of a head mount assembly used in another embodiment of the present invention.
Figure 5:
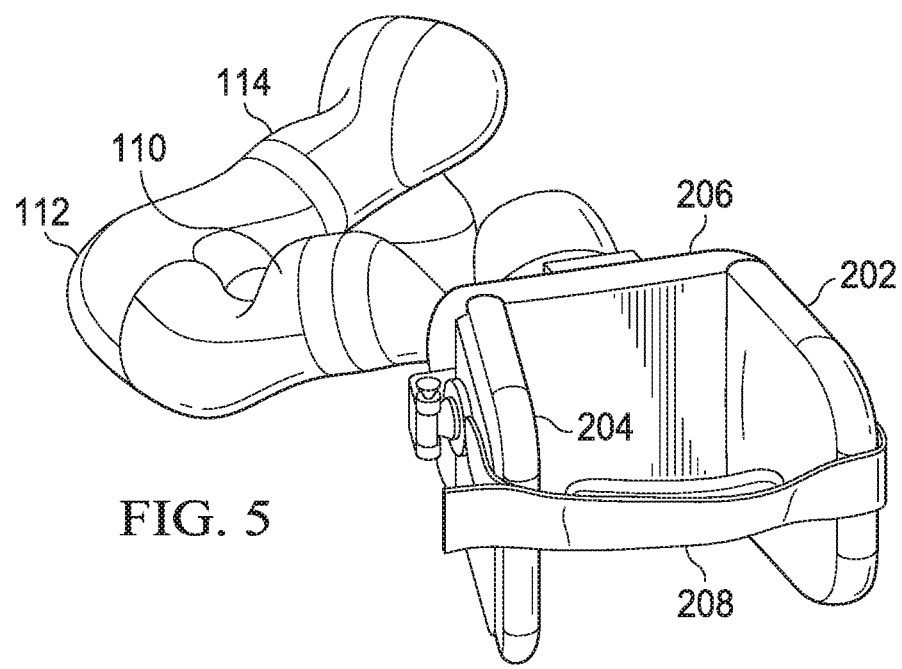
FIG. 5 illustrates another perspective view of another embodiment of a head mount assembly used in another embodiment of the present invention.

The head mount 108 can comprise any structure generally shaped to receive or partially surround a human head. FIGS. 4 and 5 depict one embodiment of a head mount. As shown therein, the head mount may include a back plate 206 that engages the back of the human head, and movable side flaps 202 and 204 that rotate inwardly and outwardly to engage with the sides of the human head. It may further include a head strap 208 affixable to the side flaps 202 and 204 that extends around the front of the human head, across the forehead. Other structures are possible that are configured to secure the human subject's head tightly enough such that movement of the head mount also moves the human subject's head.

Figure 3:
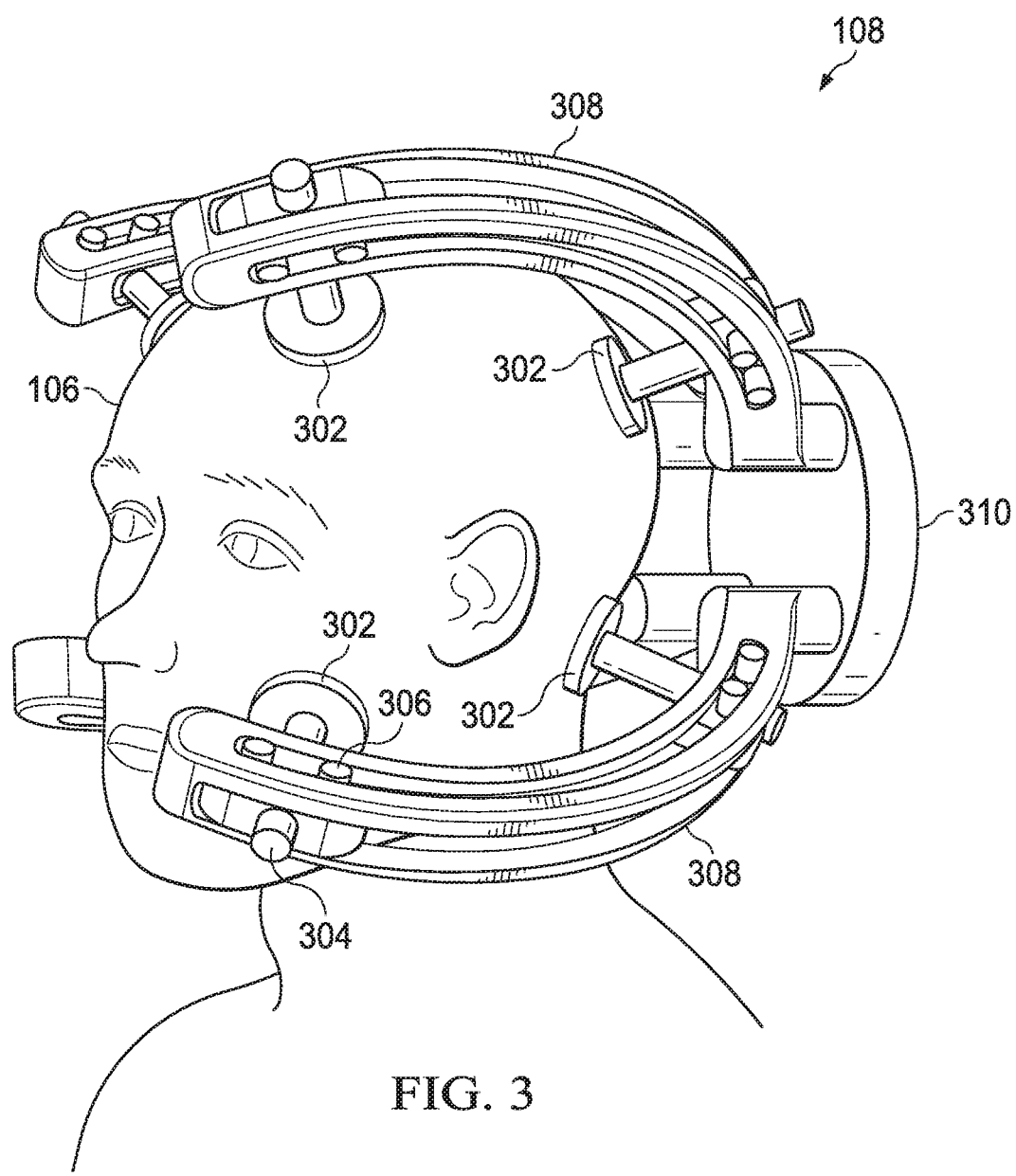
FIG. 3 illustrates a perspective view of one embodiment of a head mount assembly used in one embodiment of the present invention.

One example of another structure for a head mount is depicted in FIG. 3. As depicted therein, the head mount 108 comprises a plurality of adjustable contact pads 302. The pads can be positioned at any point along a support rail 308 by loosening a screw assembly 304, moving the pad 302, and tightening the screw assembly 304 on the rail 308. The pads 302 may also be extended towards or away from the human subject's head 106 by manipulating screw assemblies at 304 or 306. The support rails 308 extend from a hub 310. The support rails 308 are also rotatable at the point where they extend from hub 310. Hub 310 is the location that head mount 108 is affixed to the operative end of the robotic arm, by way of a mounting assembly on the back side of the hub 310 (not shown). This embodiment of the head mount is highly customizable to enhance the accuracy of the procedures, and provide increased comfort to the user.

In the embodiment depicted in FIG. 1, the human subject 104 is seated on seat 102 having a front side and a back side. The front side of the seat 102 faces a visual target screen 126. Projector 124 projects programmed images, which can be static or dynamic as desired by the practitioner, onto visual target screen 126 during the diagnosis or treatment of one or more systems of the human body, including the vestibular, ocular or proprioceptive systems. The system may comprise, instead of a projector and screen, a set of goggles worn by the human subject, which project visually discernable, pre-programmed images onto a surface in front of the human subject's eyes. The target screen may also comprise a backlit screen, such as an LCD or Plasma screen. The visual target may also comprise a shape or image projected onto a wall, or any other visually discernable target that a human subject can focus on while undergoing diagnosis or treatment.

In one embodiment, Video-Occulography (VOG) goggles may be used to track eye movements during the diagnosis or therapy method described herein below. One example of VOG goggles that can be used in conjunction with the present invention are currently sold under the EyeSeeCam trademark by EyeSeeTech GmbH of Germany. The VOG goggles may also incorporate inertial measurement capabilities, which in one embodiment are enabled by the use of one or a combination of accelerometers and gyroscopes into the goggles or associated structures. VOG goggles provide information that allows practitioners to evaluate and document eye movement physiology and disorders. Movements of the head and eyes are recorded by use of a goggle mounted with a camera and an inertial measurement sensor. Data relating to the eyes can be used to direct or coordinate movements of the robotic arm and thereby control the head position.

Data from the inertial measurement sensor, camera, and the visual stimulation parameters are measured, displayed and stored in the software used to operate the VOG goggles. The software may also calculate saccadic and smooth pursuit gain, vestibular gain (the ratio between eye and head movement velocities) and other complex information based on the raw eye-movement data. The cameras used to track eye movements are preferably infrared cameras so they can be used to detect eye movement in dark environments (such as when the lights in a room are turned off). The goggles may also include infrared light emitting diodes to light the scene and allow for accurate data gathering.

The embodiment depicted in FIG. 1 also depicts the visual target screen 126 as having a concave shape. This shape allows practitioners to display a moving visual target that does not vary (or does not significantly vary) by distance from the human subject. Other shapes are possible, including a flat visual target screen, though the strategy of the diagnosis and therapy may be varied.

The base 122 for the robotic arm is located on the back side of the seat 102. The head mount 108 can be rotated clockwise or counterclockwise at joint 110, and can be moved and positioned in three-dimensional space by actuation of the computer-controlled robotic arm comprising joints 112, 116 and 120, rotatable arm segments 114 and 118, and base 122. One example of a robotic arm that can be used in conjunction with the present invention is manufactured by Kuka Roboter Gmbh (of Augsburg, Germany) under the trademarks LBR and LWR, and described in U.S. Pat. No. 8,829,895.

A robotic arm is generally a manipulation machine that is equipped at an end distal from the base with useful tools for the automatic handling of objects, and which is programmable with respect to orientation, position, and sequence of operations in several axes of motion. The robotic arm usually comprises several members, joints, and programmable controls (control devices), which control and adjust the position and sequences of motion of the robotic arm during operation. The drives are electrical drives or drive motors, for example, and the members or arm segments run along axes that are pivotable relative to one another. A robotic arm may comprise a mechanical arm having one or more joints providing rotational motion, translation displacement, or both.

The relative position of the members that make up the robotic arm can be determined by any suitable sensor or combination of sensors, for example a combination of magnets and Hall effect sensors. The magnets can be located in one of the rotatable members, and the Hall effect sensor can be located in the adjacent rotatable member, such that the Hall effect sensor detects changes in position of the magnets on the adjacent member. In this way, the position of the robotic arm can be determined and controlled through a non-contact sensor.

A control device can be set up to evaluate the signals from the non-contacting sensor, and based upon the evaluated signals, actuate or stop the relative motion of the two members using a drive system that connects the two adjacent members.

The robotic arm used in conjunction with the present invention comprises several safety features that prevent it from causing physical harm to the human subject being treated or diagnosed. In one safety feature, the head mount can be moved in three-dimensional space to draw a virtual safety box that encompasses the comfortable range of motion for the human subject's head. During this exercise, the robotic arm can learn the boundaries of the virtual safety box by sensing the location and orientation of the head mount throughout the learning process. The control system for the robotic arm can then be programmed to restrict movement of the head mount during diagnosis or treatment to that virtual safety box defined during the learning period. The virtual safety box within which the head mount must remain can be defined as the "workspace" and the space outside the workspace can be referred to as the "protected space" because it protects the health and safety of the human subject.

Another safety feature incorporated into the robotic arm is a kinematic feedback sensor system that detects resistance to movement during diagnosis or treatment. For example, while the robot arm is programmatically moving or positioning the human subject's head in three-dimensional space, sensors in the joints and members are continuously detecting the magnitude of resistance that the human subject's head, neck and associated anatomy are exhibiting in response to movement of the head mount. If such resistance reaches or exceeds a certain threshold, a safety cutoff mechanism is engaged that either ceases treatment and stops motion of the head mount until a human technician can intercede, or returns the head mount to a "home" or "reference" position that is comfortable for the human subject being treated or diagnosed. Examples of sensors that can provide such kinematic feedback are joint torque sensors that sense resistance in all directional axes. The robotic arm can also be programmed with different resistance tolerances in each of three independent Cartesian axes, as well as different resistance tolerances with respect to changes in the orientation of the head mount attached to the distal end of the robotic arm.

Generally, the robotic arm is controlled by a computer system operatively coupled to the various sensors and drive motors embedded with the robotic arm. The position, angle of rotation, speed, and acceleration of the various robotic arm segments and attached head mount are detected using one or a combination of sensors positioned and configured for that purpose. The computer system or control module of the computer system uses positional information in a feedback, feed forward, or other combination scheme to execute the positional and rotational maneuvers and treatment methods described herein, or as desired by a practitioner of the present invention. The computer system may be controlled by any combination of input devices, including touch screens, buttons, dials and switches. The computer system may also give the practitioner information through a display screen regarding the position, speed, acceleration, or angle of rotation of the robotic arm and/or head mount.

By utilizing the described device, people with brain injuries, neurodevelopmental, neurodegenerative, or anyone looking for improved brain and body function, can benefit from the Vestibular-Ocular Reflex and Brain Rewiring therapy strategies enabled by the device. In controlling the subject's head movement in sequenced and controlled movements relative to eye fixation or active visual tracking on a target screen, healthy neural pathways can be forged and reinforced while causing the atrophy of dysfunctional neural pathways. Sensory integration can also be recalibrated. By collecting physiological data, the robot is able to algorithmically respond with methods to accelerate the effectiveness of the therapy. Cartesian direction, acceleration, deceleration, velocity, gravity compensation, vibration dampening, stiffness, force, and maximum excursion points are all programmable parameters of the robotically controlled head movements. Sequences of movements can be combined to create complex therapy sequences. Visual image target(s) on the screen can be passive or actively moving in any conceivable fashion to coordinate the therapy with the planned sequences of head movements.

For example, the robotic arm can actuate the head mount to rotate the human subject's head from left to right while the subject is asked to fixate on a non-moving target being projected on the screen in front of the chair. This type of therapy is sometimes referred to as "times one" (×1) therapy. During the head movement, data regarding the movement of the eyes and their ability to stay on target can be collected for purposes of diagnosis and treatment.

Another example of a type of therapy that is enabled by the present invention is sometimes referred to as "times two" (×2) therapy. In this type of therapy, the human subject is asked to focus on a moving target while the human subject's head is being moved by the head mount (which is actuated by the robotic arm).

Still another example of a therapy enabled by the present invention is head impulse testing. In this type of diagnostic or therapeutic application, the human subject's head is moved rapidly from one position to another, while the subject is asked to visually fixate on a stationary target projected on the screen.

The head movement precision provided by the device described herein enables practitioners to provide more reliable and effective diagnosis and treatment than was possible with the prior art. In the prior art, the times one and times two therapies were generally performed by a medical practitioner instructing the human subject to move his/her head under without any mechanical assistance. Therefore, the effectiveness of the therapy was dependent upon the human subject making accurate head movements and following the medical practitioner's instructions. Head impulse testing in the prior art involved a medical practitioner manipulating the human subject's head manually. Again, the effectiveness of this therapy was dependent on the accuracy of the medical practitioner's manual head movements. Experience shows that these methods introduce high error rates. With the present invention, by contrast, the robotic arm can reproduce the same movements to within tolerances that are unachievable in the prior art. The result is a higher success rate across all visual therapies enabled by the present invention.

Again, the potential to perform vestibular-ocular therapies in a precise and controlled manner is made technologically possible with the present invention. The idea is a novel robotic device, which uses sensors to programmatically move a human subject's head in a plane, or multiple planes of motion. In one embodiment, the invention comprises a medical device that delivers a neurologically rehabilitative therapy that helps patients with and array of disabilities and symptoms.

Features of different embodiments of the invention include: Robotic device to programmatically move a patient's head and neck across a range of 3-dimensional movements; Provide the highest degree of accuracy and safety; Multiple sensors to monitor the patient; Magnetic coupling from headgear to robot-calibrated at a specific force (ie. Newtons) as a fail safe detachment from the robotic arm; VOG Eye Tracking—3 dimensional eye tracking; Visual stimulus surrounding the patient (concave embodiment with fixed radius, or flat); Utilize a Kuka LWR robot.

Features of Programming the Movement of different embodiments of the Device include: Programming by demonstration; Programming Cartesian coordinates; Gravity compensation; Active vibration dampening (independent Cartesian x,y,z); Programmable stiffness (independent Cartesian x,y,z, and orientation); Kinematic redundancy; Programmable force.

Through VOG (video oculography) technology integration, some embodiments of the device will also be: Programmable to respond to certain eye movements, including VOR gain, Target slippage, Q Values, Latencies, Velocities; and Programmable to respond to certain physiological responses including Pupil response—dilation, constriction (mydriasis, miosis); Heart rate; Temperature changes; Perfusion index; Galvanic skin response; qEEG; other medically relevant data.

The presently disclosed and claimed system allows a practitioner to rotate a human subject's head while the human subject is contained within a human receiving area, such as being seated and restrained in a chair. The head can be rotated and moved around three different axes independently from one another and without any restriction on the number of degrees of rotation or the plane of motion. Because each axis of rotation can be programmed independently, an infinite number of acceleration vectors can be applied to the head undergoing treatment. Prior art systems are not able to accomplish this.

The device described in various embodiments herein above may be referred to as a Computer Assisted Vestibular Ocular Rehabilitation Device (CAVORD). The CAVORD provides a practitioner with consistent, precise, and reproducible therapeutic interventions while being able to monitor clinical biomarkers of accuracy, fatigue, and aberrancy. The system provides a means of exercising a subject's oculomotor, vestibular, and somatosensory systems to rehabilitate deficits that emerge during breakdown of central nervous system pathways that assist with eye tracking and head movement behavior. The device is able to monitor smoothness of movement as well as eye tracking deficits and can be programmed to implement and monitor head movements and eye tracking in any direction. This device is unique in its therapeutic and diagnostic capabilities. Some examples of its clinical applications are described below.

In order for neurons to function optimally in the human nervous system, three conditions must be met. Neurons must have oxygen, nutrition, and activation in order to maintain their connections to other neurons. Neurons must have an increase in these three factors in order to create new connections between neurons or repair damaged connections. Oxygen and nutrition are delivered to the neurons through the vascular system and their delivery is driven by the needs of the neuronal cell. A neuron uses axons and dendrites to create synapses with multiple other neurons at varying levels of proximity creating a network of communication fibers that allow cells to communicate locally and also with distal areas of the body. Due to this relationship a neuron can be stimulated by multiple connected neurons as they are activated throughout the body. These connected neurons may be linked to a peripheral receptor or another part of the central nervous system. As a neuron's activation is increased, it will make additional connections to other neurons in its network. If a neuron experiences a decrease in activation, it will begin to lose and breakdown connections to other neuronal networks. The ability of the nervous system to change and adapt to the demands of its environment is known as neuroplasticity.

The vestibular system of a human subject gives the individual a sense of their position in space and helps orient them to their environment. This system is situated in the inner ear bilaterally and is composed of two different sensory organs. The first is the semicircular canal system, which is composed of six semicircular canals. The canals are oriented with three canals on each side of the head with an orthogonal orientation to each other. Each semicircular canal is paired with a canal of opposite orientation on the other side. The two horizontal canals are oriented to sense rotations around the Z axis (vertical axis), the two anterior canals are oriented at 45 degrees to the anterior sagittal and coronal body planes and detect rotations in the vertical planes of motion, and the two posterior canals are oriented at 45 degree angles to the posterior sagittal and coronal body planes and also detect angular motion in the vertical plane. The semicircular canals are filled with fluid and angular motion is detected as this fluid puts pressure on a sensory structure called the cupula. The cupula can emit an excitatory signal or an inhibitory signal that is sent to the brain depending on the direction it is pushed. If a subject is rotated to the right, the cupula in the right horizontal canal sends an excitatory signal to the brain and the cupula in the left horizontal canal sends an inhibitory signal. This is the mechanism by which all the semicircular canal pairings function.

The second sensory organ in the vestibular system is the otolithic organ. The otolithic system is located in the inner ear bilaterally and is connected with the semicircular canal system. The otolithic organ is composed of the utricle and the saccule and senses linear translation. The organ is composed of hair cells called stereocilia in a gelatinous membrane that is weighted by calcium carbonate crystals called otoliths. When the head is placed in various positions relative to gravity or a translational stimulation is administered, the otoliths create a shearing force on the stereocilia and generate either an excitatory or inhibitory signal, which propagates through central nervous system pathways. The utricle senses linear accelerations and head-tilt in the horizontal plane while the saccule detects linear accelerations and head tilt in the vertical plane. These signals are sent from the sensing structures of the vestibular system and integrate in multiple regions of the brain and brain stem for secondary processing.

The visual system is utilized to observe the environment and generate information that assists with balance, focus, and tracking The visual system typically utilizes binocular vision with conjugate or coordinated eye movements to keep an object of interest in focus. Each eye has a retina, which contains light sensing cells that send signals to the brain to be interpreted as visual information. Within the retinal tissue is a structure called the fovea that is composed of light sensing cells responsible for color vision.

In order to maintain clear vision, the visual system must be able to keep objects of interest focused on the fovea and perform proper and coordinated movements of the eyes to keep an object in view. When the object of interest changes position or if the point of interest changes, the visual system must shift the fovea to either maintain focus or move attention to a new target. The oculomotor system assists in the task of maintaining fovealization of a target through the use of a number of eye movement strategies. These eye movement strategies form the basis for steady vision and rely on inputs and integration of information from the vestibular system, proprioceptive system, and other senses to move the eyes appropriately.

The proprioceptive system is comprised of sensors in the human body that provide information about joint angle, muscle length, and muscle tension, which is integrated to give information that identifies where body parts are in space. The system is designed to give real-time feedback about the human body's position in space and allow for appropriate actions to be taken when variables in the environment change. This system performs this through various receptors located in the joints and ligaments in the body called mechanoreceptors as well as through the muscles of the body. Skeletal muscle has two types of muscle responses, volitional and non-volitional. Volitional movements are voluntary movements of the body that are under conscious control and can be altered or planned by the human subject. Non-volitional movements are involuntary movements that are reflexive within the body. Reflexive muscle groups are responsible for maintaining posture, adapting to perturbations experienced in the environment, and activating stabilizing musculature during volitional movements.

The vascular system of the human body is designed to supply nutrients, oxygen, and other elements crucial for cellular survival throughout the body. When an increased workload is placed on a structure of the body, the vascular system will shunt blood to these areas to assist with the increased metabolic demand. As an example, when an individual uses a muscle, like performing a bicep curl, the vascular system will shunt blood to that muscle to provide additional support so the muscle can perform optimally. This helps the muscle to maximize its strength and adapt to added demand. The same mechanism is present with increased demand during activation of the central nervous system. When pathways within the nervous system are activated, more blood is shunted to those areas of activation to increase the nutrients and oxygen available for the neuronal cells.

Combinations of these systems work in conjunction with each other to ensure stable vision and that an individual has accurate interaction with their environment. The vestibulo-ocular reflex integrates information from the vestibular system and the oculomotor system, the cervico-ocular system integrates information from motion of the neck with the oculomotor system, and the vestibulocollic reflex combines information from the vestibular system and proprioceptive information from the neck. The systems described above must work in concert with each other to facilitate optimal function of the nervous system.

In order for an individual to have accurate and appropriate perception and interaction with their environment, they must have proper central integration of information coming from the vestibular system, visual system, and proprioceptive system. During periods of movement and stimulation, proper blood flow must be administered to areas of activation of the nervous system as well as to the muscles of the body. When these systems do not work in concert, breakdowns in neurologic function occur. During processes in neurodegenerative diseases or traumatic brain injury, there can be interruption of the typical pathways in the central nervous system that can cause inefficiencies in communication between areas of the brain and can distort the activation of the neuron and transport of nutrients and oxygen to parts of the brain that are in need of additional support. As these processes progress there can be continued breakdown of neural pathways with continued aberrant firing in these neural networks. In order to address these breakdowns in neural communication, stimulations can be applied to neural pathways that are found to have aberrant firing. These stimuli can be applied through sensory receptors in the body including the vestibular system, the visual system, and the proprioceptive system. The CAVORD described herein provides a means of measuring, stimulating and monitoring these pathways with a precision that has not been previously available.

When an injury or disruption to the nervous system occurs, whether from trauma, vascular accident, neurodegenerative process, or developmental aberrancy, there can be a break down in central or peripheral nervous system pathways or in end organ sensors that create a deficit in how an individual perceives their world. When this occurs, the breakdown in these pathways can be quantified through physical examination and diagnostic testing or during therapeutic intervention. Once the location of the lesion has been identified, strategies can be implemented to stimulate and rehabilitate those pathways or the end organ receptors through the use of the systems described above. The CAVORD provides a means of administering this stimulation in a highly controlled and monitored manner.

Videonystagmography (VNG) is a technology for testing inner ear and central motor functions, in a process known as vestibular assessment. It involves the use of infrared goggles to trace eye movements during visual stimulation and positional changes. Traditionally patients are asked to keep their head still during a VNG and only move their eyes according to the stimulus. The CAVORD can be used to either stabilize the head so only eye movements are being recorded or can enable the head to move freely and record those movements, allowing for novel behavior analysis opportunities.

One example of a clinical examination of human subjects who complain of dizziness is based on the head impulse test (HIT) of the vestibulo-ocular reflex (VOR). Head impulses are movements of the human subject's head that comprise small positional amplitude) (10°-25° but high acceleration ($3.000$-$6.000°/s^2$) and high velocity (150-300°/s). In the prior art, these HIT movements were performed manually by a physician, therapist, or other clinician. Oftentimes, when an examiner is administering the head impulses, they are not highly accurate in terms of correct path of impulse, acceleration, and velocity. This results in the patient having to endure many unnecessary head impulses, and more than would be required if each was administered accurately. The ability to have the CAVORD precisely and accurately deliver the head thrust is not only safer for the patient, but eliminates any unnecessary impulses the patient must endure. This saves the examiner and patient time, and the patient from unnecessary neurological fatigue and disruption.

The CAVORD is a novel medical device that adds precision and automation to standard vestibular, oculomotor, and proprioceptive rehabilitation involving movement of the head and eyes. The devise will direct rehabilitation techniques with greater accuracy, precision, speed and reproducibility than manual physician/therapist directed therapies.

Nervous system rehabilitation can involve strategies where the head and eyes of a subject are moved in a variety of directions and speeds while focusing on a target or changing the focus to different targets. The amplitude (size) of an eye/head movement should be exact in order to maximize neurological function. Manual rehabilitation therapies use an examiner or subject's perceptual choice of amplitude and speed of head and eye movements. This is inherently inaccurate and involves variability between examiners, subjects and sessions that are not in the best interest of a clinical team.

The CAVORD can establish an exact range of motion of eye-head movements and establish an appropriate velocity/speed and path of movement of the head and neck that is accurate, reproducible and safe. The CAVORD maintains that the visual target must remain in focus, not blurry, and appear stationary while the head is in motion. Eye movements are measured in real time by infrared video nystagmography allowing continuous adaptation of the velocity and speed of eye-head movements if the subject's eye slips off the target. The speed of eye-head movement may be increased as long as the target stays in focus, and slowed down to allow easier target focus. Manual procedures fail in the ability to recognize slight slippage that will confound eye-head therapies. The CAVORD corrects for this by not allowing the head to move faster than prescribed and to compensate for increased resistance or fatigue of muscles by decreasing the speed and amplitude. The computer controller for the CAVORD system senses all movement of the head via accelerometers and force sensors that are synchronized with the eye movements. An infinite number of precise diagnostic and rehabilitation strategies may be prescribed with confidence that the human subject will perform the strategy exactly as prescribed.

The CAVORD will prevent head movement while subjects perform smooth pursuits, or saccades, with eye-only strategies and allow head movement at set speeds while subjects perform smooth pursuits, or saccades, with eye-head strategies. The CAVORD will also guide the performance of visual fast movements (saccades) using an eye only, or eye-head in phase (same direction) or in counter phase (eye and head moving in opposite direction) strategies. The CAVORD is robust and can be used when the patient is in the supine, sitting or standing positions. Thus, the human receiving area of the system can be, without limitation, a platform (possibly raised or height-adjustable), a seat, or standing base. In other embodiments, it also can be used when the patient is moving as an integral adjunct to gait retraining The CAVORD maximizes the improvement of a subject's central nervous system or brain's compensation for injuries or abnormalities within the vestibular or balance system by using exact information specific to an exercise or rehabilitation strategy. Traditional manual therapies or subject-directed rehabilitations are compromised because of the inherent error involved in estimating a range of motion or speed of the head, neck or eye. The brain interprets information gained from the vestibular or balance system. When there is an injury or abnormality in any portion of this system, the brain must be retrained or taught to interpret correctly the information it receives. Rehabilitative exercises of the vestibular system, the oculomotor system, and the proprioceptive system stimulate receptors in the body and the CAVORD maintains an exact, controlled environment to stimulate these systems. This stimulation produces information to be processed by the brain. Accuracy and reproducibility of these exercises is essential for the brain to learn to tolerate and accurately interpret this stimulation. The CAVORD can teach the brain to adapt to all stimuli, increasing performance and compensation for any abnormal stimulus that might be encountered.

The sensors in the CAVORD allow an exact range of movement of the neck and head at a speed that will be exact and guaranteed. Human subjects can be trained to bend the head and look at a variety of targets that are accurately placed. While repeating the strategy, the patient and clinical staff are guaranteed that the rehabilitation will be reproducible with the ability to initiate change in procedure instantaneously. Accurate performance equates with faster and more consistent improvements.

CAVORD allows accurate movement at speeds that can be changed dynamically or programmatically. Typical vestibular rehabilitation can begin with eye-head movement that is slow, followed by movement at increased speed. A human subject might not obtain the exact desired side-to-side speed when attempting exercise by themselves or with a therapist. CAVORD maintains an exact speed of movement and will adapt to the subject's ability or stop the session if it senses increased resistance of neck muscles or fatigue of eye movements (neurological fatigue).

Individuals diagnosed or suspected of having neurological conditions often have dysfunction in different facets of neural processing. Some individuals have inaccuracies in the ability to detect and/or transfer sensory signals to be sent to central processors. Others may have difficulty in their ability to receive these signals and process them in an accurate, timely manner. Still others may have errors in converting sensory stimuli into central integration to be executed as accurate appropriate movement, cognition, emotion or effect by the individual. Oftentimes, people with neurological dysfunction have combinations of these processing errors that culminate in the conventional diagnostic criteria that are commonplace in the practice of health care.

Utilization of CAVORD may be beneficial for those suffering with these types of disorders as the stimulation dosage and type may be manipulated to adapt or modify these errors in neural processing to improve the functionality of the system. Implementing this type of stimulation has the potential of driving positive neuroplastic changes within the central nervous system.

Disorders that may benefit from this intervention include, but are not limited to, the following classifications based on the current nomenclature and diagnostic criteria:

Balance disorders are a common manifestation of vestibular, visual, and proprioceptive deficit. Stimulation of these systems can be utilized to rehabilitate numerous conditions that affect peripheral as well as central manifestations of these disorders. Positive neuroplastic changes can be made through the use of CAVORD in these cases. Some of these cases include: Dysequilibrium, Mal De Débarquement, Motion-sickness, Pre-syncope, and Vertigo.

Deficiencies of gaze and eye movements are very common signs of dysfunction in a number of pathological- and trauma-oriented conditions. Stimulation of the vestibular, oculomotor, and proprioceptive pathways can aid greatly in addressing the central issue causing the ocular dysfunction. CAVORD allows for therapies to be implemented that can specifically address the planes and locations in which these dysfunctions occur. This is accomplished by programming the CAVORD with specific eye and head movements that will stimulate central visual, central vestibular, or central proprioceptive pathways that correlate to the eye and head movements where pathology is present. Some of these conditions include: Convergence Insufficiency, Convergence Spasm, Diplopia, and Dysjunctive Eye Movements.

Developmental delay is a condition that affects millions of children. As the human body is early in development, it uses stimuli from its environment to mold and form its perception and understanding of the world around it. When a child misses establishment of specific connections in the brain, significant delays or deficits can arise that will hinder the child from engaging in an appropriate or typical way. Senses and systems like the vestibular system, the visual and oculomotor system, and the proprioceptive system can be used as access points to the central nervous system to provide increased stimulation to areas of the brain that are experiencing aberrant development or delay. This added stimulation can help increase integration of areas of the brain connected to these systems and drive developmental processes toward a more typical development pathway. Some of these conditions include: Alexia, Attention Deficit Hyperactivity Disorder (ADD/ADHD), Autism Spectrum Disorders, Dyslexia, Obsessive Compulsive Disorder (OCD), Oppositional Defiant Disorder (ODD), Pervasive Developmental Disorder (PDD)/—Not Otherwise Specified (NOS), and Social Communication Disorder (SCD).

Dysautonomia is a condition where there is dysregulation of the cardiovascular system. This may manifest as irregularities, acceleration, or deceleration of the heartbeat, abnormal blood flow and perfusion to tissues in the body (peripheral and central), and hypersensitivity to touch. The cardiovascular system is regulated by central nervous system connections in the brain and brainstem. These regions have crossover connections with regions that integrate with the vestibular, oculomotor, and proprioceptive systems. By this mechanism, CAVORD can make an impact therapeutically with this population of individuals. Some conditions that can be affected through this approach include: Cardiac Arrhythmia, Reflex Sympathetic Dystrophy, Reynaud's Phenomenon, and Tachycardia.

Movement disorders are highly prevalent conditions of human subjects associated with neurological conditions that affect the speed, fluency, quality, and ease of movement.

Abnormal fluency or speed of movement may involve excessive or involuntary movement (hyperkinesia) or slowed or absent voluntary movement (hypokinesia). These conditions affect the function of and are consequences of aberrancies in the visual, oculomotor, vestibular and somatosensory systems of human subjects. CAVORD can be used to drive positive neuroplastic changes that can address these types of issues. Movement disorders include, but are not limited to: Abulia/dysbulia, Akinetic/Rigid Syndromes, Aphasia/dysphasia, Apraxia/dyspraxia, Ataxia/dystaxia, Bradykinetic Syndromes, Dyskinesias, Dystonias, Myoclonus, Spasticity, Stereotypic Movement Disorder, Tic/Tourette's Syndrome, and Tremor.

Neurodegenerative disorders include a range of conditions that cause damage largely within the neurons of the brain and spinal cord. Degeneration of these neurons can result in the inability of different regions of the brain to operate and communicate with other regions and pathways of the brain. The effects are far-reaching and though the function of one area of the brain may not be directly related to another area, damage in the shared communication networks can provide a mechanism for massive functional loss. While neurodegenerative conditions cause damage to neurons that may be irreplaceable, surviving neurons may provide alternative communication through creation of new connections to other neuronal networks (synaptogenesis). CAVORD is a powerful means to drive this connectivity. Some neurodegenerative disorders that may benefit from this therapy include: Alzheimer's Disease, Coritcobulbar Degeneration, Dementia, Multiple Sclerosis, Multiple System Atrophy, Parkinson's Disease/Parkinson-Plus/Atypical Parkinson's, and Supranuclear Palsy.

Orthostatic intolerance is a condition where specific positions of the body cause an excessive increase, decrease, or fluctuations in blood pressure or heart rate. As an individual moves from a lying position or seated position to a standing position, the brain will sense a drop in blood pressure through baroreceptors or a change in position through the otolithic system, and make compensatory changes to keep blood perfusion to the entire body as constant and consistent as possible. In an individual who has sustained an injury to the body that affects this system, it can cause extreme shifts of blood pressure or heart rate. One mechanism to rehabilitate this system is the use of vestibular input through the otolithic system to recalibrate the system so changes of position do not elicit an aberrant response from the body. Another mechanism is through the oculomotor system where specific eye and head movements can be utilized to rehabilitate areas in the brain that share common integration points with areas of the brain that control blood pressure and heart rate. The CAVORD is a means of providing this stimulation in a manner that is specific to the injury that has occurred. Applicable conditions include Orthostatic Hypotension, and Positional Orthostatic Tachycardic Syndrome (POTS).

Pain syndromes include those conditions associated with abnormal perception of nociception leading to suffering in an individual. Pain is a complex phenomenon that has a multitude of origins. Pain as a central consequence is problematic for individuals as well as healthcare providers in the sense that the pain generator is due to a faulty perception of sensory stimuli. This perception occurs as an inaccuracy in central processing within the brain. These central processing systems have shared neural networks with the vestibular, oculomotor, and proprioceptive systems. In this sense, CAVORD can be used in a therapeutic approach to decrease the impact of these types of conditions. Pain syndromes include, but are not limited to: Cervicalgia, Cluster Headache, Complex Regional Pain Syndrome (CRPS), Head pain, Lumbalgia, Migraine, Temperomandibular Joint Disorder, Thoracalgia, and Trigeminal Neuralgia.

Traumatic brain injury is a condition that can have profound impact on an individual's nervous system and sensing organs. Traumatic injury can occur to any region of the brain. The systems affected can be wide-ranging or focal in their distribution or presentation. When these deficits are quantified, a determination of the regions of the brain affected can be made. If the injury affects the vestibular system, visual system, oculomotor system, somatosensory system, the vascular system, or any system in communication with these systems, a therapy regimen utilizing CAVORD may be used to rehabilitate the damaged areas of the brain. Some of these conditions include: Centrally-maintained Vestibulopathy, Mild, Moderate, Severe Traumatic Brain Injury, Post-concussive Syndrome, and Stroke.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

What is claimed is:

1. A method of treating at least one system of a human subject comprising:
   arranging the human subject within a human receiving area facing a visual target;
   securing a head mount to the human subject's head, wherein the head mount is affixed to and actuated by a distal end of a robotic arm, wherein the distal end is opposite of a base of the robotic arm;
   actuating the head mount to move the human subject's head in three dimensional space while the human subject focuses on the visual target, wherein the robotic arm comprises a sensor system that detects resistance to movement in each of three independent Cartesian axes during said actuating;
   measuring eye movements and adapting speed or amplitude of said actuating based on said measuring eye movements;
   compensating for increases in said resistance by decreasing speed or amplitude of said actuating; and
   engaging a safety cutoff mechanism if said resistance reaches or exceeds a threshold.

2. The method of claim 1 wherein the system is a vestibular system.

3. The method of claim 1 wherein the system is a visual system.

4. The method of claim 1 wherein the system is a proprioceptive system.

5. The method of claim 1 wherein the visual target is stationary during the actuating.

6. The method of claim 1 wherein the visual target is moving during the actuating.

7. The method of claim 1 further comprising the step of collecting data indicative of the position or movement of the human subject's eyes.

8. The method of claim 1 further comprising the step of collecting data indicative of the position or movement of the human subject's head.

9. The method of claim 1 wherein the system is at least one of a vestibular system, a visual system, and a proprioceptive system.

10. The method of claim 1 wherein the human subject is seated during the method.

* * * * *